United States Patent
Cruise et al.

(10) Patent No.: US 11,883,564 B2
(45) Date of Patent: Jan. 30, 2024

(54) ANTIMICROBIAL COATINGS

(71) Applicant: MicroVention, Inc., Aliso Viejo, CA (US)

(72) Inventors: Gregory M. Cruise, Rancho Santa Margarita, CA (US); Steve Plotkin, Beaumont, CA (US); Petr Vasek, Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 5 days.

(21) Appl. No.: 17/388,734

(22) Filed: Jul. 29, 2021

(65) Prior Publication Data

US 2022/0031914 A1 Feb. 3, 2022

Related U.S. Application Data

(60) Provisional application No. 63/058,980, filed on Jul. 30, 2020.

(51) Int. Cl.
| | | |
|---|---|---|
| *A61L 29/08* | (2006.01) | |
| *A61L 29/04* | (2006.01) | |
| *A61L 29/06* | (2006.01) | |
| *A61M 25/00* | (2006.01) | |
| *A61L 29/16* | (2006.01) | |

(52) U.S. Cl.
CPC .......... *A61L 29/085* (2013.01); *A61L 29/043* (2013.01); *A61L 29/044* (2013.01); *A61L 29/06* (2013.01); *A61L 29/16* (2013.01); *A61M 25/0017* (2013.01); *A61L 2300/104* (2013.01); *A61L 2300/114* (2013.01); *A61L 2300/254* (2013.01); *A61L 2300/406* (2013.01); *A61L 2420/08* (2013.01)

(58) Field of Classification Search
CPC ........ A61L 29/085; A61L 31/10; A61L 31/14; A61L 27/54
See application file for complete search history.

(56) References Cited

U.S. PATENT DOCUMENTS

| | | |
|---|---|---|
| 8,263,720 B1 | 9/2012 | Salamone et al. |
| 2002/0094322 A1 | 7/2002 | Lawson et al. |
| 2009/0324666 A1* | 12/2009 | Krongauz ............... A61L 27/54 424/409 |
| 2010/0113871 A1 | 5/2010 | Dias et al. |
| 2013/0323291 A1* | 12/2013 | Li ........................ A61L 31/14 524/502 |
| 2018/0325649 A1* | 11/2018 | Wu ........................ A61L 31/10 |

FOREIGN PATENT DOCUMENTS

WO 2022/026689 A1 2/2022

OTHER PUBLICATIONS

International Search Report and Written Opinion, dated Nov. 2, 2021, for International Application No. PCT/US2021/043677 filed on Jul. 29, 2021.

* cited by examiner

*Primary Examiner* — Dah-Wei D. Yuan
*Assistant Examiner* — Andrew J Bowman
(74) *Attorney, Agent, or Firm* — K&L Gates LLP; Brian J. Novak; Benjamin D. Heuberger

(57) ABSTRACT

Described are coatings for medical devices and methods of forming same.

18 Claims, No Drawings

ANTIMICROBIAL COATINGS

CROSS-REFERENCE TO RELATED APPLICATIONS

This application claims the benefit of U.S. provisional patent application Ser. No. 63/058,980, filed Jul. 30, 2020, the entire disclosure of each of which is incorporated herein by reference.

FIELD

Described herein are coatings for medical devices.

BACKGROUND

Urinary catheters are tubular devices that are widely used to manage incontinence and retention of urine. While these catheters are highly effective at managing the flow of urine out of the body, they are prone to bacterial infection and encrustation. These complications limit the duration of catheterization and increase health care costs.

SUMMARY

This disclosure relates to the preparation and use of durable, anti-microbial coatings for medical devices. In some embodiments, the coatings are UV-cured. In some embodiments, the coatings can be for use with lumens, for example catheters and microcatheters, to be used inside the urinary tract. The antimicrobial coating enables the long-term use of catheters inside the urinary tract.

Coatings described herein can comprise multiple coating layers, for example two coating layers, for example a base coat and a top coat. The base coat functions as a "tie" layer between the polymer of the catheter, typically a silicone or latex, and the top coat. The base coat is designed to adhere to the catheter and provide binding sites for the attachment of the top coat. The top coat is designed to adhere to the base coat and enhance the antimicrobial nature of the catheter. In embodiments, the top coat can be any synthetic or naturally-occurring small molecule, protein, glycosaminoglycan, or polymer.

Disclosed embodiments comprise an antimicrobial coating formulation comprising a base coat comprising a copolymer of tetrahydrofurfuryl acrylate and a monomer comprising a functional group amenable to further derivatization, wherein the copolymer is modified to contain a plurality of reactive moieties; and a top coat comprising at least one antimicrobial compound, a polymer, or a combination thereof.

In embodiments, the coating functional groups can be, for example, at least one of hydroxyl, amine, and carboxylic acid groups, such as at least one of hydroxyethyl methacrylate, hydroxyethyl acrylate, hydroxypropyl acrylate, hydroxypropyl methacrylate, hydroxybutyl acrylate, hydroxybutyl methacrylate, N-(3-aminopropyl) methacrylamide, 2-aminoethyl methacrylate, 2-aminoethyl methacrylamide, acrylic acid, methacrylic acid, beta-carboxyethyl acrylate, combinations thereof, and derivatives thereof.

In embodiments, the antimicrobial compound can be an antimicrobial small molecule, protein, polysaccharide, glycosaminoglycan, or polymer derivatized with polymerizable groups.

In embodiments, the antimicrobial compound can be silver-containing polymers, antibiotics, antimicrobial peptides, zwitterionic polymers, nitric oxide releasing polymers, enzymes, extremely hydrophilic polymers, and extremely hydrophobic polymers. The antimicrobial coating can be of a linear or branched structure.

Further embodiments include a method of preparing an antimicrobial-coated catheter comprising forming a base coat by dissolving two or more monomers and an initiator in a solvent; polymerizing the monomers to form a copolymer; adding a reactive group to the copolymer to form a derivatized copolymer; forming a top coat by dissolving two or more monomers and an initiator in a solvent; applying the base coat to the catheter; and applying the top coat to the catheter. In embodiments, the solvent can be at least one of benzene, toluene, xylene, dimethylformamide, dimethyl sulfoxide, dioxane, 2-methyltetrahydrofuran, anisole, benzonitrile, chlorinated aromatic solvents, diisopropyl ether, diglyme, butanol, and combinations thereof.

Further embodiments comprise a method of preparing an antimicrobial-coated catheter comprise initiating polymerization by at least one of a reduction-oxidation, radiation, or heat. In embodiments the initiator comprises azobisisobutyronitrile (AIBN) or a water soluble AIBN derivative (2,2'-azobis(2-methylpropionamidine) dihydrochloride), or 4,4'-azobis(4-cyanopentanoic acid), N,N,N',N'-tetramethylethylenediamine, ammonium persulfate, benzoyl peroxides, and combinations thereof including azobisisobutyronitriles. In embodiments the initiator is present at about 0.25% to about 2% w/w of the mass of the monomers in solution. In embodiments the radiation initiation is applied with infrared, ultraviolet or visible light.

In embodiments comprising a method of preparing an antimicrobial-coated catheter, a reactive group is added to the copolymer to form a derivatized copolymer.

Further embodiments include a catheter comprising an antimicrobial coating formulation comprising: a base coat comprising a copolymer of tetrahydrofurfuryl acrylate and a monomer comprising a functional group amenable to further derivatization, wherein the copolymer is further modified to contain a plurality of reactive moieties; and a top coat comprising at least one antimicrobial compound, a polymer, or a combination thereof.

In embodiments the catheter is a urinary catheter.

DETAILED DESCRIPTION

Device Coatings

Embodiments disclosed herein comprise coatings. In some embodiments, these coatings can be for medical devices such as, but not limited to, medical lumens, catheters, and microcatheters. In some embodiments, the coatings can be anti-microbial.

In one embodiment, the coatings can be for urinary catheters. These catheters are typically formed of silicones, latexes, poly(vinyl chloride), and copolymers thereof and derivatives thereof. The coating can comprise two layers; a base coat can adhere to the polymeric substrate of the catheter and provide binding sites for a top coat.

a. Base Coat

In some embodiments, the base coat polymer comprises a copolymer of tetrahydrofurfuryl acrylate and at least one other monomer with functional groups capable of further chemical reaction such as hydroxyl, amine, and carboxylic acid groups. Suitable monomers containing hydroxyl groups comprise hydroxyethyl methacrylate, hydroxyethyl acrylate, hydroxypropyl acrylate, hydroxypropyl methacrylate, hydroxybutyl acrylate, hydroxybutyl methacrylate, combinations thereof, and derivatives thereof. Suitable monomers containing amine groups comprise N-(3-aminopropyl) methacrylamide, 2-aminoethyl methacrylate, 2-aminoethyl methacrylamide, combinations thereof, and derivatives thereof. Suitable monomers containing carboxylic acids comprise acrylic acid, methacrylic acid, beta-carboxyethyl acrylate, combinations thereof, and derivatives thereof.

In embodiments, to prepare the copolymer, the two or more monomers and an initiator are dissolved in a solvent. In general, any solvent that dissolves the two or more monomers and the initiator can be used. Suitable solvents comprise benzene, toluene, xylene, dimethylformamide, dimethyl sulfoxide, dioxane, 2-methyltetrahydrofuran, anisole, benzonitrile, chlorinated aromatic solvents, diisopropyl ether, diglyme, butanol, and combinations thereof.

In embodiments, polymerization initiators can be used to start the polymerization of the monomers in the solution. The polymerization can be initiated by reduction-oxidation, radiation, heat, or any other method known in the art. Radiation polymerization of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In one embodiment, the polymerization initiator comprises azobisisobutyronitrile (AIBN) or a water soluble AIBN derivative (2,2'-azobis(2-methylpropionamidine) dihydrochloride), or 4,4'-azobis(4-cyanopentanoic acid). Other initiators can comprise N,N,N',N'-tetramethylethylenediamine, ammonium persulfate, benzoyl peroxides, and combinations thereof, including azobisisobutyronitriles. In embodiments, concentrations of the initiator can range from about 0.25% to about 2% w/w of the mass of the monomers in solution. For example, the initiator concentration can be 0.25%, 0.5%, 1%, 1.5%, 2%, or the like.

Disclosed base coat polymerization reactions can be performed at elevated temperatures, preferably in the range from about 65 to about 85° C. After the polymerization is completed, the copolymer is recovered by precipitation in a non-solvent and dried under vacuum. In embodiments, the resulting copolymer has a molecular weight between about 15,000 and about 350,000 g/mole. In some embodiments, the molecular weight is between about 25,000 and about 100,000 g/mole, when analyzed by gel permeation chromatography with polystyrene standards.

Following polymerization, reactive groups, preferably acrylates and/or methacrylates, are added to the copolymer via the hydroxyl, amine, and/or carboxylic acid groups of the second or more monomer. In general, the derivatization compound can be a heterobifunctional compound. One moiety reacts with the hydroxyl, amine, and/or carboxylic acid groups of the copolymer. The other moiety is an acrylate or methacrylate group.

Derivatization compounds can comprise 2-isocyanatoethyl acrylate, 2-isocyanatoethyl methacrylate, acrylic acid N-hydroxysuccinimide ester, methacrylic acid N-hydroxysuccinimide ester, hetero-bifunctional poly(ethylene glycol) with acrylate and isocyanate groups, combinations thereof, and derivatives thereof.

To prepare the derivatized copolymer, the copolymer, derivatization compound, and any catalyst are dissolved in a solvent. In general, any solvent that dissolves the two or more monomers and the initiator can be used. Solvents comprise dimethyl formamide, dimethyl sulfoxide, toluene, acetone, acetonitrile, N,N-dimethylacetamide, N-methyl-2-pyrrolidone, and combinations thereof.

When reacting a derivatization with a nucleophilic group of the base coat copolymer, the molar equivalent of the derivatization agent ranges from about 5% to about 80% of the available nucleophilic groups. In some embodiments, the molar equivalent of the derivatization agent ranges from about 10% to about 50% of the available nucleophilic groups, for example 10%, 20%, 30%, 40%, or 50%. This level of derivatization corresponds to a range of about 4 to about 50 reactive groups per molecule. Additionally, in embodiments the addition of a Lewis base as a catalyst can be used. Lewis bases can comprise, for example, triethylamine and pyridine, typically in a concentration of about 1% to about 10% of the moles of the derivatization compound added. The reaction proceeds at ambient or elevated temperature, such as 30° C., 40° C., or 45° C. After the derivatization is complete, the completed, decorated copolymer is recovered by precipitation in a non-solvent and dried under vacuum.

Top Coat

The top coat can comprise an anti-microbial small molecule, protein, polysaccharide, glycosaminoglycan, or polymer derivatized with polymerizable groups. The top coat can be any naturally-occurring or synthetic compound, derivatives thereof and combinations thereof. The structure of the top coat can be linear or branched, including graft, star, comb, brush, and dendrimer structures.

Disclosed examples of suitable top coats comprise silver-containing polymers, antibiotics, antimicrobial peptides, zwitterionic polymers (such as phosphorylcholine containing polymers and sulfobetaine containing polymers), nitric oxide-releasing polymers, enzymes, extremely hydrophilic polymers, and extremely hydrophobic polymers.

Silver is an effective and well-studied antimicrobial agent. While effective, silver is readily oxidized to silver ions and prevents long-term antimicrobial activity. In embodiments, polymers and copolymers containing silver as well as moieties to couple to the base coat can serve as antimicrobial top coats.

Antibiotics are a well-studied class of small molecules that have antimicrobial activity. While effective, bacteria can develop resistance to antibiotics. This can prevent multiple uses of antibiotic-coated urinary catheters. Suitable antibiotics comprise nitrofural, sparfloxacin, minocycline, rifampin, triclosan, and chlorhexidine. Antibiotics as well as polymers and copolymers containing antibiotics as well as moieties to couple to the base coat can serve as antimicrobial top coats.

Antimicrobial peptides are oligomers of amino acids that have antimicrobial activity. Unlike antibiotics, these peptides are relatively unstudied. In embodiments, antimicrobial peptides coupled to the base coat can serve as antimicrobial top coats.

Zwitterionic polymers are polymers that include an equal number of positive and negative electric charges, resulting in a net neutral compound. These polymers are anti-fouling due to their electrostatic and steric repulsion properties. Zwitterionic polymers evaluated for use in urinary catheters comprise phosphorylcholine, sulfobetaine, and carboxybetaines. Over time, these anti-fouling properties lose effectiveness. A zwitterionic polymer or copolymer containing moieties to couple to the base coat can serve as antimicrobial top coats in disclosed embodiments.

In addition to naturally occurring compounds, synthetic copolymers can be synthesized to create top coats with antimicrobial activity. In general, a first component of the copolymer is a compound to increase the antimicrobial activity of the catheter surface. A second component contains a polymerizable acrylate or methacrylate as well as an amine, carboxylic acid, or hydroxyl group. Monomers containing amines comprise 3-aminopropyl methacrylamide, 2-aminoethyl methacrylate, N-(3-methylpyridine)acrylamide, 2-(N,Ndimethylamino)ethyl methacrylate, 2-(N,N-dimethylamino)ethyl acrylate, 2-(tertbutylamino)ethyl methacrylate, methacryloyl-L-lysine, N-(2-(4-aminopheny 1)ethy 1)acry lamide, N-(4-amino benzy 1)acry lamide, and N-(2-(4-imidazoly I)ethy I)acry lamide, derivatives thereof, and combinations thereof. Monomers including carboxylic acids comprise acrylic acid, methacrylic acid, derivatives thereof, and combinations thereof. Monomers containing hydroxyl groups comprise 2-hydroxyethyl acrylate, 2-hydroxyethyl methacrylate, 2-hydroxypropyl acrylate, 4-hydroxybutyl acrylate, derivatives thereof, and combinations thereof.

In embodiments, to prepare the polymer, the two or more monomers and an initiator are dissolved in a solvent. In general, any solvent that dissolves the two or more monomers and the initiator can be used. Solvents can comprise methanol/water, ethanol/water, isopropanol/water, dioxane/water, tetrahydrofuran/water, dimethylformamide/water, dimethyl sulfoxide and/or water, and combinations thereof. With carboxylic acid and hydroxyl containing monomers, a wider range of solvents can be utilized, including toluene, xylene, dimethyl sulfoxide, dioxane, tetrahydrofuran, methanol, ethanol, and dimethyl formamide.

Polymerization initiators can be used to start the polymerization of the monomers in the solution. The polymerization can be initiated by reduction-oxidation, radiation, heat, or any other method known in the art. Radiation polymerization of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In one embodiment, the polymerization initiator is azobisisobutyronitrile (A TRN) or a water soluble AIBN derivatives (2,2'-azobis(2-methylpropionamidine) dihydrochloride), or 4,4'-azobis(4-cyanopentanoic acid). Other initiators can comprise N,N,N',N'-tetramethylethylenediamine, ammonium persulfate, benzoyl peroxides, and combinations thereof, including azobisisobutyronitriles. Concentrations of the initiator can range from about 0.25% to about 2% w/w of the mass of the monomers in solution.

The polymerization reaction can be performed at elevated temperatures, such as in the range from about 65 to about 85° C. For example, in embodiments the polymerization reaction is performed at 65° C., 70° C., 75° C., 80° C., or 85° C. After the polymerization is completed, the polymer is recovered by precipitation in a non-solvent and dried under vacuum. The molecular weight of the copolymer can range from about 500 g/mole to about 100,000 g/mole, or from about 1,000 g/mole to about 40,000 g/mole.

In embodiments, the base coat copolymer can have a characteristic viscosity when dissolved in solvent. Base coat copolymer dissolved in propylene glycol monomethyl ether acetate at 15% w/w can have viscosity ranging from about 2 cP (centipoise) to about 15 cP. In some embodiments, viscosity range can be from about 6 cP to about 13 cP.

An option for the first component is zwitterionic monomers, i.e. monomers containing an equal number of positive and negative charges to have overall neutral charge. Due to the charges, zwitterionic compounds can tightly bind water and reduce protein conformation change. In one embodiment, the zwitterionic monomer is 2-methacryloyloxyethyl phosphorylcholine, as shown in the structure below.

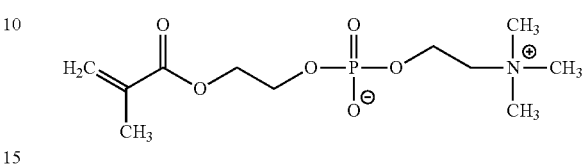

Additionally, monomers synthesized from betaines, i.e. carboxylbetaines, phosphobetaines, and sulfobetaines) are preferred zwitterionic monomers. An example of such a monomer is [2-(Methacryloyloxy)ethyl]dimethyl-(3-sulfopropyl)ammonium hydroxide, as shown in the structure below.

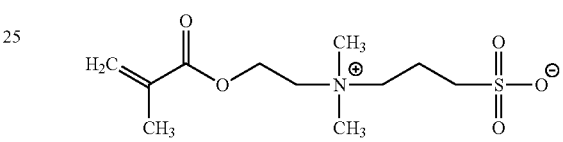

In embodiments, the first component comprises monomers that release nitric oxide. Nitric oxide is a known antimicrobial agent. Molecules containing (meth)acrylates and nitric oxide releasing chemistry such as diazeniumdiolate or S-nitrosothiol can be synthesized and subsequently polymerized into copolymers.

In embodiments, another option for the first component is the use of very hydrophobic polymers/copolymers. Hydrophobic surfaces have been shown to delay attachment of bacteria. Hydrophobic monomers comprise n-octadecylacrylamide, tert-butyl methacrylate, n-hexyl acrylate, phenyl methacrylate, methyl styrene, derivatives thereof, and combinations thereof.

In disclosed embodiments, following the selection of the top coat base, reactive groups, such as acrylates and/or methacrylates, are added to the polymer via any convenient reactive moiety, such as hydroxyls, amines, or carboxylic acids, with a derivatization compound. In general, the derivatization compound can be a hetero-bifunctional compound. One moiety reacts with the hydroxyl, amine, and/or carboxylic acid groups of the copolymer. The other moiety is an acrylate or methacrylate group. Derivatization compounds can comprise acryloyl chloride, methacryloyl chloride, 2-isocyanatoethyl acrylate, 2-isocyanatoethyl methacrylate, acrylic acid N-hydroxysuccinimide ester, methacrylic acid Nhydroxysuccinimide ester, hetero-bifunctional poly(ethylene glycol) with acrylate and isocyanate groups, combinations thereof, and derivatives thereof.

In embodiments, to prepare the derivatized polymer, the polymer, derivatization compound, and any catalyst are dissolved in a solvent. In general, any solvent that dissolves the top coat polymer, derivatization agent, and the initiator can be used. Solvents can comprise aromatic and chlorinated solvents, including benzene, toluene, xylene, dichloromethane, chloroform, and combinations thereof.

When reacting a derivatization agent with a reactive moiety of the top coat polymer, the target derivatization can correspond to less than 2 groups per molecule. Additionally, the addition of a Lewis base as a catalyst can be used. Lewis bases can comprise triethylamine and pyridine, typically in a concentration of about 1% to about 10%, or about 2% to about 9%, or about 4% to about 7%, of the moles of the derivatization compound added. The reaction proceeds at room temperature. After the derivatization is complete, the activated polymer is recovered by precipitation in a nonsolvent and dried under vacuum.

Top coat polymers can have a characteristic viscosity when dissolved in solvent. Top coat polymer dissolved in methanol at 25% w/w can have viscosity ranging from about 2 cP to about 15 cP. In some embodiments, viscosity range can be from about 6 cP to about 13 cP, or 8 cP to 11 cP, or the like.

Base Coat Solutions

After the base coat polymer is synthesized it is incorporated into a base coat solution. The base coating solution can comprise the solvent, base coat copolymer, initiator and optionally a surfactant. In general, any solvent or mixtures of solvents may be utilized, provided that the components can be dissolved into the solvent or solvent mixtures. Suitable solvents comprise water, alcohols, glycol ethers, aromatics, polar aprotic solvents, methanol, ethanol, isopropyl alcohol, 2-ethoxy ethanol, propylene glycol monomethyl ether acetate, benzene, toluene, xylene, dimethyl formamide, dimethyl sulfoxide, and combinations thereof. The base coat copolymer is dissolved into the selected solvent at a concentration ranging from about 0.2% w/w to about 35% w/w. Preferred concentration range is 0.7% to 1.2% w/w.

In one embodiment, initiators comprise Norrish Type I initiators, Norrish Type II initiators, and combinations thereof. The initiator concentration in the solvent ranges from about 0.1% to about 6%, or about 0.5%. Examples of suitable Norrish Type I or free-radical photo-initiators are benzoin derivatives, methylolbenzoin and 4-benzoyl-1,3-dioxolane derivatives, benzilketals, α,α-dialkoxyacetophenones, α-hydroxy alkylphenones, aaminoalkylphenones, acylphosphine oxides, bisacylphosphine oxides, acylphosphine sulphides, halogenated acetophenone derivatives, and the like. Commercial examples of suitable Norrish Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone) (Ciba-Geigy), Irgacure 184 (1-hydroxy-cyclohexyl-phenyl ketone as the active component (Ciba-Geigy), Darocur 1173 (2-hydroxy-2-methyl-1-phenylpropan-1-one as the active component) (Ciba-Geigy), Irgacure 907 (2-methyl-1-[4-(methylthio)phenyl]-2-morpholino propan-1-one) (Ciba-Geigy), Irgacure 369 (2-benzyl-2-dimethylamino-1-(4-morpholinophenyl)-butan-1-one as the active component) (Ciba-Geigy), Esacure KIP 150 (poly{2-hydroxy-2-methyl-1-[4-(Imethylvinyl)phenyl]propan-1-one}) (Fratelli Lamberti), Esacure KIP 100 F (blend of poly {2-hydroxy-2-methyl-1-[4-(1-methylvinyl)phenyl]propan-1-one} and 2-hydroxy-2-methyl-1-phenyl-propan-1-one) (Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide, and methylbenzophenone derivatives) (Fratelli Lamberti), acylphosphine oxides such as Lucirin TPO (2,4,6-trimethylbenzoyl di phenyl phosphine oxide) (BASF), Irgacure 819 (bis(2,4,6-trimethylbenzoyl)-phenylphosphine-oxide) (Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-I-one) (Ciba-Geigy), and the like. Also, mixtures of type I photo-initiators can be used.

Norrish Type II photo-initiators that can be used in disclosed medical coating formulations can comprise aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photo initiators.

In embodiments, the base coat coating solution may also contain a surfactant. In general, any surfactant may be used. Disclosed surfactants suitable for use comprise sodium lauryl sulfate, Tween 20, Span 80, Triton X-100, Pluronic F68, Pluronic L-81, combinations thereof, and derivatives thereof. The optional surfactant is dissolved into the selected solvent at a concentration ranging from 0.08% w/w to 15% w/w.

Top Coat Solutions

Next, the top coat solution is prepared. In embodiments, the top coating solution is comprised of the solvent, top coat polymer, initiator and optionally a surfactant. In general, any solvent or mixtures of solvents may be utilized, provided that the components can be dissolved into the solvent or solvent mixtures. In embodiments, suitable solvents comprise water, alcohols, glycol ethers, aromatics, polar aprotic solvents, and combinations thereof. Preferred solvents comprise methanol, ethanol, isopropyl alcohol, 2-ethoxy ethanol, propylene glycol monomethyl ether acetate, benzene, toluene, xylene, dimethyl formamide, dimethyl sulfoxide, acetonitrile, and combinations thereof. The top coat polymer is dissolved into the selected solvent at a concentration ranging from 5% w/w to 75% w/w or more, depending on the desired viscosity of the top coat solution. A preferred concentration of top coat copolymer is 29% w/w.

Initiators can comprise Norrish Type I initiators, Norrish Type II initiators, and combinations thereof. The initiator concentration in the solvent ranges from about 0.1% w/w to about 6% w/w, preferably about 0.3% w/w. Examples of suitable Norrish Type I or free-radical photo-initiators are benzoin derivatives, methylolbenzoin and 4-benzoyl-1,3-dioxolane derivatives, benzilketals, α,α-dialkoxyacetophenones, α-hydroxy alkylphenones, α-aminoalkyiphenones, acylphosphine oxides, bisacylphosphine oxides, acylphosphine sulphides, halogenated acetophenone derivatives, and the like.

Other suitable Norrish Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone) (Ciba-Geigy), Irgacure 184 (1-hydroxycyclohexyl-phenyl ketone as the active component) (Ciba-Geigy), Darocur 1173 (2-hydroxy-2-methyl-1-phenylpropan-1-one as the active component) (Ciba-Geigy), Irgacure 907 (2-methyl-1-[4-(methylthio)phenyl]-2-morpholino propan-1-one) (CibaGeigy), Irgacure 369 (2-benzyl-2-dimethylamino-1-(4-morpholinophenyl)-butan-1-one as the active component) (Ciba-Geigy), Esacure KIP 150 (poly {2-hydroxy-2-methyl-1-[4-(1-methylvinyl)phenyl]propan-1-one}) (Fratelli Lamberti), Esacure KIP 100 F (blend of poly{2-hydroxy-2-methyl-1-[4-(1-methylvinyl)phenyl]propan-1-one} and 2-hydroxy-2-methyl-1-phenyl-propan-1- one) (Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide, and methylbenzophenone derivatives) (Fratelli Lamberti), acylphosphine oxides such as Lucirin TPO (2,4,6-trimethylbenzoyl di phenyl phosphine oxide) (BASF), Irgacure 819 (bis(2,4,6-trimethylbenzoyl)-phenylphosphine-oxide) (Ciba-Geigy), Irgacure 1700 (25:75% blend of bis(2,6-dimethoxybenzoyl)-2,4,4-trimethyl-pentyl phosphine oxide, and 2-hydroxy-2-methyl-1-phenyl-propan-1-one) (Ciba-Geigy), and the like. Also, mixtures of type I photo-initiators can be used.

Norrish Type II photo-initiators that can be used comprise aromatic ketones such as benzophenone, xanthone, derivatives of benzophenone (e.g. chlorobenzophenone), blends of benzophenone and benzophenone derivatives (e.g. Photocure 81, a 50/50 blend of 4-methyl-benzophenone and benzophenone), Michler's Ketone, Ethyl Michler's Ketone, thioxanthone and other xanthone derivatives like Quantacure ITX (isopropyl thioxanthone), benzil, anthraquinones (e.g. 2-ethyl anthraquinone), coumarin, or chemical derivatives or combinations of these photoinitiators.

In embodiments, the top coat coating solution may also contain a surfactant. In general, any surfactant may be used. Suitable surfactants can comprise sodium lauryl sulfate, Tween 20, Span 80, Triton X-100, Pluronic F68, Pluronic L-81, combinations thereof, and derivatives thereof. The optional surfactant is dissolved into the selected solvent at a concentration ranging from about 0.08% w/w to about 5% w/w.

Coating Medical Devices a. Base Coat Application

Turning to the process of applying the base coat and top coat to a catheter, in embodiments the catheter is first cleaned by a solvent wipe to remove any gross contamination from its surface. In general, any solvent can be used if it does not dissolve or degrade the catheter shaft. Such solvents can comprise glycol ethers, methyl ethyl ketone, chlorinated solvents, tetrahydrofuran, hexane, ethyl acetate and acetone. Following solvent cleaning, the catheter shaft can be plasma treated to further clean its surface. Plasmas derived from various gases can be used, but preferred gases are argon and oxygen. In some embodiments, both argon and oxygen plasmas may be utilized. With the catheter suitability cleaned, it is ready to be coated.

Sequential application and UV curing of the base coat followed by top coat to a selected urinary catheter can be done with a Harland PCX coating machine or equivalent. In embodiments, the coating machine is charged with base coat and top coat solutions. Next, the urinary catheter is placed in the coating machine above the coating solutions. The coating machine first dips the catheter into a tube filled with base coat. The catheter is then extracted at a constant rate of about 0.1 to about 10.0 cm/sec, such as about 5.0 cm/sec. After extraction, the catheter is exposed to ultraviolet radiation with a wavelength ranging from about 10 nm to about 400 nm. Combinations of wavelengths in this range will also provide a suitably cured base coat. Preferred wavelengths comprise about 254 nm and about 365 nm. The base coat cure time ranges from about 0.1 min to about 6 min such as about 0.5 min. After the base coat is cured, the coating machine dips the catheter into the top coat solution.

a. Top Coat Application

The catheter is then extracted at a constant rate of about 0.1 cm/sec to about 10.0 cm/sec, or at 0.6 cm/sec. Finally, the top coat is exposed to ultraviolet radiation ranging from about 10 nm to about 400 nm, or combinations of wavelengths in this range. Preferred wavelengths to suitably cure the top coat comprise about 254 nm and about 365 nm. The top coat cure time ranges from about 0.1 minutes to about 6 minutes, in some embodiments, about 5.5 minutes. The coating process is complete after the top coat cure time has elapsed.

In embodiments, following the coating process, the catheter may be washed in a solvent bath to remove unbound coating components such as initiator and surfactant. Any solvent may be used that does not degrade the coating or catheter. Suitable solvents can comprise ethanol, methanol, acetone, acetonitrile, propylene glycol methyl ether acetate, and combinations thereof. Catheters are washed by soaking in selected solvent for time ranging from 1 minute to 15 minutes. In embodiments, a preferred time is 5 minutes.

EXAMPLE 1

Preparation of a Base Coat Polymer

Tetrahydrofurfuryl acrylate (80.0 g), 18.5 g of 4-hydroxybutyl acrylate and 250 mL of toluene are combined in 1 L round bottom flask. That solution is de-gassed by purging argon gas through for 30 min. Then, 1.0 gram AIBN initiator is added, the mixture is purged with argon for another 10 min, and the flask is immersed in an 80° C. oil bath and reflux condenser with argon inlet is attached. The mixture is then heated for 16 hours under argon.

The reaction is cooled down and precipitated with 1.2 L of cold MTBE, precipitated product—viscous polymer is collected and dried at vacuum. Typical yield is 85-95%. Dried polymer is dissolved in dry DMF (200 mL, ~0.5 g/mL) and treated with 0.84 mL of triethylamine and 3.0 mL of 2-isocyanatoethyl acrylate, mixture is heated to 45° C. for 5 hrs. Polymer is precipitated out with 1.2 L of cold MTBE, washed 2×200 mL of MTBE and dried at high vacuum.

EXAMPLE 2

Preparation of Liquid Base Coat Solution

Polymer from Example 1, 5.2 g, is dissolved in 500.0 mL of propylene glycol monomethyl ether acetate, then 0.18 g Pluronic L-81 surfactant, 140 mg of benzophenone, and 140 mg 1-hydroxycyclohexyl phenyl ketone are added. Complete dissolution with shaking for 30 minutes produces a clear, homogeneous solution.

EXAMPLE 3

Preparation of a Decorated Top Coat Macromere

A mixture of 106.71 g (382 mmol) of [2-(Methacryloyloxy)ethyl]dimethyl-(3-sulfopropyl)ammonium hydroxide (DMAPS) and 13.84 g (96.8 mmol) of 4-Hydroxybutyl acrylate (HBtAc) is dissolved in 150 mL of 1,4-Dioxane and 150 mL of water in 1 L RB flask. AIBN (0.75 g) is added and water-cooled condenser is attached. The flask is immersed into a pre-heated oil bath at 75° C. and the mixture is stirred for 16 hours. The cooled reaction mixture is poured into 1.2 L of mixture of hexane:2-propanol (3:1), and the precipitated product is collected, washed one time with 200 mL of hexane:2-propanol mixture, two times with 200 mL of hexane, separated and dried in vacuum.

Resulting material-DMAPS-HBtAc co-polymer is dissolved in anhydrous DMF (200 mL), Triethylamine (2.68 mL, 19.2 mmol) followed by 2-Isocyanatoethyl acrylate (2.40 ml, 19.2 mmol) are added and the reaction is stirred for 16 hours at ambient temperature.

The product is obtained by precipitation from 1.2 L of MTBE, washed 2 times with 200 ml of MTBE, separated and dried in vacuum.

EXAMPLE 4

Preparation of a Top Coat Solution

Decorated DMAPS-HBtAc top coat macromer (200.0 g) is dissolved in 500 mL of methanol. Then, 1.5 g of benzophenone and 1.5 g of 1-hydroxycyclohexyl phenyl ketone are added. Complete dissolution after shaking for 1 minute results in a clear, homogenous solution.

EXAMPLE 5

Coating Microcatheter with a Top Coat Solution

A Harland PCX 175 Coating machine is charged with the base coat and top coat solutions prepared in Examples 2 and 4, respectively. A urinary catheter is prepared for coating by first wiping the outer surface with acetone. The catheter is then plasma treated with argon plasma (365 sccm, 300 watts, 500 mtorr) followed by oxygen plasma (120 sccm, 150 watts, 400 mtorr). The catheter is then affixed in the coating machine and coated using an automated, pre-programmed recipe. The sequential stepwise process dips the catheter in base coat solution, extracts it at 5 cm/sec, UV cures the base coat for 30 sec (365 nm λ, 60.0 mJ UV dose), dips the catheter in top coat solution, extracts it at 6 cm/sec, and finally cures the top coat for 330 sec (365 nm λ, 660.0 mJ UV dose).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An antimicrobial coating formulation, comprising:
a base coat comprising a copolymer of tetrahydrofurfuryl acrylate and a monomer comprising a functional group amenable to further derivatization, wherein the copolymer is further modified to contain a plurality of reactive moieties; and
a top coat comprising at least one antimicrobial compound, a polymer, or a combination thereof, wherein the top coat comprises a copolymer reaction product of a mixture comprising [2-(methacryloyloxy)ethyl]dimethyl-(3-sulfopropyl)ammonium hydroxide and 4-hydroxybutyl acrylate, and the top coat comprises a decorated top coat formed from a reaction product of a mixture comprising the co-polymer reaction product and 2-isocyanatoethyl acrylate.

2. The antimicrobial coating formulation of claim 1, wherein the top coat comprises a top coat macromer formed from a reaction product of a mixture comprising the decorated top coat, benzophenone, and 1-hydroxycyclohexyl phenyl ketone.

3. The antimicrobial coating formulation of claim 1, wherein the base coat comprises a copolymer of tetrahydrofurfuryl acrylate and 4-hydroxybuyl acrylate.

4. The antimicrobial coating formulation of claim 3, wherein the base coat comprises a reaction product of a mixture comprising the copolymer, benzophenone, and 1-hydroxycyclohexyl phenyl ketone.

5. The antimicrobial coating formulation of claim 1, wherein said functional group comprises at least one of hydroxyl, amine, or carboxylic acid group.

6. The antimicrobial coating formulation of claim 1, wherein said monomer comprises hydroxyethyl methacrylate, hydroxyethyl acrylate, hydroxypropyl acrylate, hydroxypropyl methacrylate, hydroxybutyl acrylate, hydroxybutyl methacrylate, N-(3-aminopropyl) methacrylamide, 2-aminoethyl methacrylate, 2-aminoethyl methacrylamide, acrylic acid, methacrylic acid, beta-carboxyethyl acrylate, or a combination thereof.

7. The antimicrobial coating formulation of claim 1, wherein said antimicrobial compound comprises an antimicrobial small molecule, protein, polysaccharide, glycosaminoglycan, or polymer derivatized with polymerizable groups.

8. The antimicrobial coating formulation of claim 1, wherein said antimicrobial compound comprises at least one of silver-containing polymers, antibiotics, antimicrobial peptides, zwitterionic polymers, nitric oxide releasing polymers, enzymes, extremely hydrophilic polymers, and extremely hydrophobic polymers.

9. The antimicrobial coating formulation of claim 1, wherein the structure of said top coat is linear or branched.

10. A catheter, comprising a surface including the antimicrobial coating formulation of claim 1.

11. A catheter, comprising a surface including the antimicrobial coating formulation of claim 2.

12. A catheter, comprising a surface including the antimicrobial coating formulation of claim 3.

13. A catheter, comprising a surface including the antimicrobial coating formulation of claim 4.

14. A catheter, comprising a surface including the antimicrobial coating formulation of claim 5.

15. A catheter, comprising a surface including the antimicrobial coating formulation of claim 6.

16. A catheter, comprising a surface including the antimicrobial coating formulation of claim 7.

17. A catheter, comprising a surface including the antimicrobial coating formulation of claim 8.

18. A catheter, comprising a surface including the antimicrobial coating formulation of claim 9.

* * * * *